US011986800B2

(12) United States Patent
Liang et al.

(10) Patent No.: US 11,986,800 B2
(45) Date of Patent: May 21, 2024

(54) OCM CATALYST COMPOSITION HAVING IMPROVED STABILITY AND CARBON EFFICIENCY

(71) Applicant: SABIC GLOBAL TECHNOLOGIES, B.V., Bergen Op Zoom (NL)

(72) Inventors: Wugeng Liang, Sugar Land, TX (US); Dick Nagaki, Sugar Land, TX (US); Yu-Lun Fang, Sugar Land, TX (US); David West, Sugar Land, TX (US)

(73) Assignee: SABIC GLOBAL TECHNOLOGIES, B.V., Bergen op Zoom (NL)

( * ) Notice: Subject to any disclaimer, the term of this patent is extended or adjusted under 35 U.S.C. 154(b) by 221 days.

(21) Appl. No.: 17/785,216

(22) PCT Filed: Nov. 10, 2020

(86) PCT No.: PCT/US2020/059840
§ 371 (c)(1),
(2) Date: Jun. 14, 2022

(87) PCT Pub. No.: WO2021/126414
PCT Pub. Date: Jun. 24, 2021

(65) Prior Publication Data
US 2023/0030055 A1 Feb. 2, 2023

Related U.S. Application Data

(60) Provisional application No. 62/949,463, filed on Dec. 18, 2019.

(51) Int. Cl.
*B01J 23/10* (2006.01)
*B01J 21/04* (2006.01)
(Continued)

(52) U.S. Cl.
CPC ............... *B01J 23/10* (2013.01); *B01J 21/04* (2013.01); *B01J 37/0201* (2013.01);
(Continued)

(58) Field of Classification Search
CPC . B01J 23/002; B01J 23/10; B01J 21/04; B01J 37/0201; B01J 37/088;
(Continued)

(56) References Cited

U.S. PATENT DOCUMENTS 5,043,505 A 8/1991 Erekson et al.
5,712,217 A 1/1998 Choudhary et al.
(Continued)

FOREIGN PATENT DOCUMENTS

EP 0335130 A1 10/1989
EP 3194070 A2 7/2017
(Continued)

OTHER PUBLICATIONS

Office Action dated Dec. 8, 2021, U.S. Appl. No. 16/821,409, filed Mar. 17, 2020.
(Continued)

*Primary Examiner* — In Suk C Bullock
*Assistant Examiner* — Jason Y Chong
(74) *Attorney, Agent, or Firm* — Rodney B. Carroll; Conley Rose, P.C.

(57) ABSTRACT

The invention relates to a composition containing a catalyst having high catalytic stability for conducting oxidative coupling of methane (OCM) at high carbon efficiency, while improving both methane and oxygen conversion. Particularly, the inventive catalyst is a metal oxide supported catalyst, which contains an alkali metal promoter and a mixed metal oxide component having at least one alkali earth metal and at least one rare earth metal. The metal oxide support is selected in a manner, such that at least a portion
(Continued)

of the metal oxide support is capable of reacting with at least a part or whole of the alkali metal promoter under conditions of calcination during catalyst preparation. The invention further provides a method for preparing such a metal oxide supported catalyst composition, using a calcination process. Additionally, the invention further describes a process for producing $C_{2+}$ hydrocarbons, using such a catalyst composition.

6 Claims, 4 Drawing Sheets

(51) Int. Cl.
  *B01J 37/02* (2006.01)
  *B01J 37/08* (2006.01)
  *C07C 2/84* (2006.01)
(52) U.S. Cl.
  CPC .............. *B01J 37/088* (2013.01); *C07C 2/84* (2013.01); *C07C 2521/04* (2013.01); *C07C 2523/02* (2013.01); *C07C 2523/10* (2013.01)
(58) Field of Classification Search
  CPC .............. B01J 2523/00; B01J 2523/02; B01J 2523/10; C07C 2/84; C07C 2521/04
  See application file for complete search history.

(56) References Cited

U.S. PATENT DOCUMENTS

| | | | |
|---|---|---|---|
| 6,087,545 | A | 7/2000 | Choudhary et al. |
| 9,963,402 | B2 | 5/2018 | Cizeron et al. |
| 11,439,984 | B2 | 9/2022 | Liang et al. |
| 11,541,375 | B2 * | 1/2023 | Liang ................... C01G 41/006 |
| 2007/0083073 | A1 | 4/2007 | Bagherzadeh et al. |
| 2013/0023709 | A1 | 1/2013 | Cizeron et al. |
| 2016/0074844 | A1 | 3/2016 | Freer et al. |
| 2016/0107143 | A1 | 4/2016 | Schammel et al. |
| 2017/0014807 | A1 | 1/2017 | Liang et al. |
| 2017/0267605 | A1 | 9/2017 | Tanur et al. |
| 2018/0118637 | A1 | 5/2018 | Zurcher et al. |
| 2019/0077728 | A1 | 3/2019 | Cizeron et al. |
| 2019/0233364 | A1 | 8/2019 | Lange De Oliveira et al. |

FOREIGN PATENT DOCUMENTS

| | | |
|---|---|---|
| RU | 2144844 C1 | 1/2000 |
| RU | 2306177 C2 | 9/2007 |
| RU | 2435830 C1 | 12/2011 |
| RU | 2523013 C1 | 7/2014 |
| RU | 2783516 C1 | 11/2022 |
| WO | 03024595 A1 | 3/2003 |
| WO | 2013177461 A1 | 11/2013 |
| WO | 20180085820 A1 | 5/2018 |
| WO | 20180175535 A1 | 9/2018 |
| WO | 201604442 A2 | 11/2018 |
| WO | 20180213183 A1 | 11/2018 |
| WO | 2019048404 A1 | 3/2019 |
| WO | 2021080716 A1 | 4/2021 |
| WO | 2021080717 A1 | 4/2021 |
| WO | 2021126414 A1 | 6/2021 |

OTHER PUBLICATIONS

Choudhary, Vasant R. et al., "Coupling of Exothermic and Endothermic Reactions in Oxidative Conversion of Natural Gas into Ethylene/Olefins over Diluted SrO/La2O3/SA5205 Catalyst", Industrial & Engineering Chemistry Research, 1997, pp. 3520-3527, vol. 36, No. 9, American Chemical Society.

Mulla, S.A.R et al., "Oxidative conversion of ethane to ethylene over supported SrO-promoted Er2O3 catalyst", Journal of Molecular Catalysis A: Chemical, 2004, pp. 259-262, vol. 223, Elsevier B.V.
Choudhary, Vasant R. et al., "Oxidative Coupling of Methane over a Sr-Promoted La2O3 Catalyst Supported on a Low Surface Area Porous Catalyst Carrier", Industrial & Engineering Chemistry Research, 1997, pp. 3594-3601, vol. 36, No. 9, American Chemical Society.
Choudhary, Vasant R. et al., "Oxidative Coupling of Methane over Supported La2O3 and La-Promoted MgO Catalysts: Influence of Catalyst-Support Interactions", Industrial & Engineering Chemistry Research, 1997, pp. 2096-2100, vol. 36, No. 6, American Chemical Society.
Choudhary, V.R. et al., "Oxidative Coupling of Methane over SrO Deposited on Different Commercial Supports Precoated with La2O3", Industrial & Engineering Chemistry Research, 1998, pp. 2142-2147, vol. 37, No. 6, American Chemical Society.
Mulla, S.A.R. et al., "Conversion of ethane to ethylene in presence of limited O2 over supported SrO promoted Sm2O3 catalyst", Indian Journal of Chemical Technology, Nov. 2003, pp. 615-618, vol. 10.
Asami, Kenji et al., "Selective Oxidative Coupling of Methane over Supported Lead Oxide Catalyst," Chemistry Letters, 1986, pp. 1233-1236, The Chemical Society of Japan.
Uphade, B.S. et al., "Influence of metal oxide-Support interactions in supported la-promoted CaO catalysts for oxidative coupling of methane," Studies in Surface Science and Catalysis, 1998, pp. 1015-1021, vol. 113, Elsevier B.V. (Abstract Only).
Bytyn, W. et al., "Supported PbO catalysts for the oxidative coupling of methane—The effect of surface acidity of the support on C2+ selectivity," Applied Catalysis, 1986, pp. 199-207, vol. 28, Elsevier B.V. (Abstract Only).
Fang, Xueping et al., "Oxidative Coupling of Methane on W-Mn Catalysts," Journal of Molecular Catalysis, 1992, pp. 255-261, vol. 8, No. 4.
Fang, Xueping et al., "Preparation and Characterization of Catalyst for Oxidative Coupling of Methane," Journal of Molecular Catalysis, 1992, pp. 427-433, vol. 6, No. 6.
Lee, Jong Yeol et al., "Scaled-up production of C2 hydrocarbons by the oxidative coupling of methane over pelletized Na2WO4/Mn/SiO2 catalysts: Observing hot spots for the selective process," Fuel, 2013, pp. 851-857, vol. 106, Elsevier Limited.
Arndt, Sebastian et al., "Mn—Na2WO4/SiO2 as Catalyst For The Oxidative Coupling of Methane. What is Really Known?," Applied Catalysis A: General, 2012, pp. 53-61, vols. 425-426, Elsevier.
Foreign Communication from Related Application—International Search Report and Written Opinion of the International Searching Authority, International Application No. PCT/US2020/051725, dated Sep. 21, 2020, 8 pages.
Foreign Communication from Related Application—International Search Report and Written Opinion of the International Searching Authority, International Application No. PCT/US2020/051724, dated Jan. 22, 2021, 8 pages.
Foreign Communication from Related Application—International Search Report and Written Opinion of the International Searching Authority, International Application No. PCT/US2020/059840, dated Apr. 28, 2021, 13 pages.
Office Action issued on corresponding Russian Application dated Oct. 6, 2022, regarding Russian Application No. 2022113196, filed May 17, 2022, 24 pages.
Foreign Communication from Related Counterpart—Decision to Grant dated Oct. 27, 2022, Russian Application No. 2022113297, filed Sep. 21, 2020, 20 pages.
Filing Receipt, Specification and Drawings for U.S. Appl. No. 17/769,879, filed Apr. 18, 2022, entitled "Multilayer Mixed Oxide Supported Catalyst for Oxidative Coupling of Methane," 45 pages.
Filing Receipt, Specification and Drawings for U.S. Appl. No. 17/769,884, filed Apr. 18, 2022, entitled "Multilayer Mixed Oxide Supported Catalyst for Oxidative Coupling of Methane," 45 pages.

* cited by examiner

OCM CATALYST COMPOSITION HAVING IMPROVED STABILITY AND CARBON EFFICIENCY

CROSS REFERENCE TO RELATED APPLICATIONS

This application is a filing under 35 U.S.C. 371 of International Application No. PCT/US2020/059840 filed Nov. 10, 2020, entitled "OCM Catalyst Composition Having Improved Stability and Carbon Efficiency" which claims priority to U.S. Provisional Application No. 62/949,463 filed Dec. 18, 2019, which applications are incorporated by reference herein in their entirety.

FIELD OF INVENTION

The invention relates to the field of catalyst compositions used for the oxidative coupling of methane (OCM).

BACKGROUND

Methane is a widely available feedstock and if oxidatively coupled, in presence of certain methane coupling catalysts, commercially high value chemicals, such as ethylene and other $C_{2+}$ hydrocarbons, can potentially be produced at high production margins. However, one of the reasons why oxidative coupling of methane has not been commercially exploited so far for the production of ethylene and other $C_{2+}$ hydrocarbons, is because the process of oxidative coupling of methane (OCM) results in low carbon efficiency as the desired $C_{2+}$ hydrocarbons on being produced tend to be oxidized to the more thermodynamically favored carbon dioxide ($CO_2$). Carbon dioxide once formed cannot be recycled efficiently for further use in the OCM process and therefore regarded as a waste by-product. Although carbon monoxide is also generated as a by-product during the OCM reaction, carbon monoxide is not considered as a waste by-product as it can be recycled back to methane using the methanation reaction (Eqn I) as shown below.

$$CO + 3H_2 \rightarrow CH_4 + H_2O \quad (I)$$

Thus, unlike selectivity towards carbon dioxide, selectivity towards the carbon monoxide may be considered favorably while determining the overall process carbon efficiency. One way to improve carbon efficiency and promote higher selectivity towards $C_{2+}$ hydrocarbons is by using alkali metal based promoters such as sodium. It is believed that alkali metals on account of their strong basicity can assist in mitigating the formation of certain intermediate oxide species such as oxidized methyl radicals, which promote the formation carbon dioxide and other undesirable product intermediates. As a result, the use of alkali metal promoters in OCM catalysts have been found to improve carbon efficiency and selectivity of an OCM process.

However, a limitation associated with alkali metal promoters in OCM catalyst, is that alkali metals have their melting point of around 800° C.-900° C., which is close to or lower than the usual temperature conditions at which OCM reactions are conducted. As a consequence, alkali metal promoters tend to evaporate gradually from the catalyst system and its beneficial influence on catalyst performance gradually diminishes with time on stream. In certain instance as evidenced from the results of Reference 1 and Reference 2 of this disclosure, the presence of sodium promoters although imparts excellent catalyst performance initially, with increased time on stream, catalyst performance notably, the methane and oxygen conversion deteriorates rendering such ordinary sodium promoted catalysts unviable for commercial application in OCM process. Previous attempts to find suitable solutions for improving $C_{2+}$ hydrocarbon selectivity and carbon efficiency in OCM processes, have been described in various scientific and patent literature such as the teachings provided in the publication by Hiyoshi et.al (Fuel Processing Technology, Volume 133, May 2015, Page 29-34: *Oxidative coupling of methane over alkali chloride—Mn—$Na_2WO_4/SiO_2$ catalysts: Promoting effect of molten alkali chloride*). Although the results reported appear promising, there is still room for further improvement in developing better and improved OCM catalyst systems, having one or more benefits of having (i) high carbon efficiency and $C_{2+}$ hydrocarbon selectivity, and (ii) increased catalyst stability along with improved methane conversion and oxygen conversion.

SUMMARY

A solution to some or all of the drawbacks and limitations described above, resides in the present inventive composition containing an OCM catalyst. Accordingly, the present invention relates to a composition, comprising a catalyst represented by a general formula: $[(AM_z)_{1-e}AE_aRE1_bRE2_cAT_dO_x)][(M_mO_n)_f(AM_z)_e]$  $[M_mO_n]_{1-f}$ wherein, (i) 'AM' represents an alkali metal, wherein the alkali metal is selected from the group consisting of sodium, potassium, rubidium and caesium; (ii) 'AE' represents an alkaline earth metal; (iii) 'RE1' represents a first rare earth element; (iv) 'RE2' represents a second rare earth element; (v) 'AT' represents a third rare earth element 'RE3', or a redox agent 'RX' selected from antimony, tin, nickel, chromium, molybdenum, tungsten, manganese, bismuth; wherein, 'a', 'b', 'c', 'd' and 'z' each independently represent relative molar ratio; wherein 'a' ranges from about 0.1 to about 5; 'b' ranges from about 0.01 to about 10; 'c' ranges from 0 to about 10; 'd' ranges from 0 to about 10; 'z' ranges from about 0.01 to about 10; 'x' balances the oxidation state; wherein, the first rare earth element, the second rare earth element and the third rare earth element, are different; (vi) $M_mO_n$ represents a metal oxide catalyst support, which is not chemically associated with the alkali metal 'AM', wherein 'M' is a metal capable of forming an oxide reaction product on reacting with the alkali metal 'AM' under conditions of calcination, 'm' ranges from about 1 to about 5, and 'n' ranges from about 1 to about 5; and (vii) $(M_mO_n)_f(AM_z)_e$ represents an oxide reaction product produced, when a portion of the metal oxide support ($M_mO_n$) reacts with some or all of the alkali metal 'AM', wherein 'e' and 'f' are variables that signify the partial association of the metal oxide support $M_mO_n$ with the alkali metal 'AM', with 'e' ranging from greater than zero to less than or equal to 1 (i.e. 0<e≤1) and 'f' ranging from greater than zero to less than 1 (i.e., 0<f<1).

In some embodiments of the invention, the relative molar ratio 'z' ranges from about 0.8 to about 5. In some embodiments of the invention, the alkali metal 'AM' is sodium. In some embodiments of the invention, the alkaline earth metal 'AE' is selected from the group consisting of magnesium, calcium, strontium, barium, and combinations thereof. In some preferred embodiments of the invention, the alkaline earth metal 'AE', is strontium. In some other embodiments of the invention, the first rare earth element 'RE1', the second rare earth element 'RE2', and the third rare earth element 'RE3', are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In some embodiments of the invention, the metal 'M' of the metal oxide catalyst support $M_mO_n$ is selected from aluminum, zinc, tin (II), and lead (II).

In some embodiments of the invention, the metal oxide catalyst support $M_mO_n$ is aluminum oxide ($Al_2O_3$). In some preferred embodiments of the invention, the alkaline earth metal 'AE' is strontium, the first rare earth element 'RE1' is lanthanum, the second rare earth element 'RE2' is neodymium, the third rare earth element 'RE3' is ytterbium and the metal oxide support is aluminum oxide ($Al_2O_3$). In some embodiments of the invention, the catalyst of the general formula, is represented by the empirical formula $Na_zSr_aLa_bNd_cYb_dO_x/Al_2O_3$, wherein 'a' ranges from about 0.1 to about 2; 'z' ranges from about 0.1 to about 8; 'b' ranges from about 0.6 to about 5; 'c' ranges from greater than zero to about 5; and 'd' ranges from about greater than zero to about 0.4. In some preferred embodiments of the invention, the catalyst of general formula, is represented by the empirical formula $Na_{4.0}Sr_{0.5}La_{1.8}Nd_{0.7}Yb_{0.1}O_x/Al_2O_3$. In some preferred embodiments of the invention, the catalyst of the general formula is represented by the empirical formula $Na_{1.0}Sr_{0.5}La_{1.8}Nd_{0.7}Yb_{0.1}O_x/Al_2O_3$. It should be understood that where actual metals are shown rather than the variable symbols AM, AE, RE1, RE2, and AT, such formulas are empirical, provided however, that the partitioning of the alkali metal between the support $M_mO_n$ and the other components is still present as expressed in the general formula. In this way, these empirical formulas fall within the general formula and although the $Al_2O_3$ is shown alone, there is always some alkali metal associated with it. This is supported by data provided in the specification below.

In some aspects of the invention, the invention provides a method for preparing the composition containing the catalyst of the present invention, the method comprising: (a) impregnating an alkali metal impregnated metal oxide support with an aqueous solution of a mixed metal oxide precursor and forming a supported catalyst precursor, and (b) calcining the supported catalyst precursor at a temperature of at least 800° C. and for at least 1 hour, and forming the composition. In some preferred embodiments of the invention, the aqueous solution of the mixed metal oxide precursor, comprises at least one compound containing an alkaline earth metal 'AE' and at least one compound containing a first rare earth element 'RE1'. In some embodiments of the invention, the aqueous solution of the mixed metal oxide precursor, comprises at least one compound containing an alkaline earth metal 'AE', at least one compound containing a first rare earth element 'RE1', at least one compound containing a second rare earth element 'RE2' and at least one compound containing a third rare earth element 'RE3'. In some embodiments of the invention, the alkali metal impregnated metal oxide support is prepared by a method comprising the steps of: (a) impregnating a metal oxide support with a solution comprising an alkali metal compound and forming an alkali metal impregnated metal oxide support precursor; (b) calcining the alkali metal impregnated metal oxide support precursor at a temperature of at least 800° C. and for at least 1 hour, and forming the alkali metal impregnated metal oxide support.

In some aspects of the invention, the invention describes a process for preparing a $C_{2+}$ hydrocarbon mixture product comprising (a) introducing a feed mixture comprising methane and oxygen in a reactor containing the composition comprising the catalyst of the present invention made by any of the methods provided in paragraph [0009]; (b) subjecting the feed mixture to a methane coupling reaction under conditions suitable to produce the $C_{2+}$ hydrocarbon mixture product; and (c) recovering the $C_{2+}$ hydrocarbon mixture product after removing unconverted methane from the $C_{2+}$ hydrocarbon mixture product. In some embodiments of the invention, the feed mixture has a methane to oxygen molar ratio ranging from about 2:1 to about 15:1.

Other objects, features and advantages of the invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from some specific embodiments may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION

Figure 1:
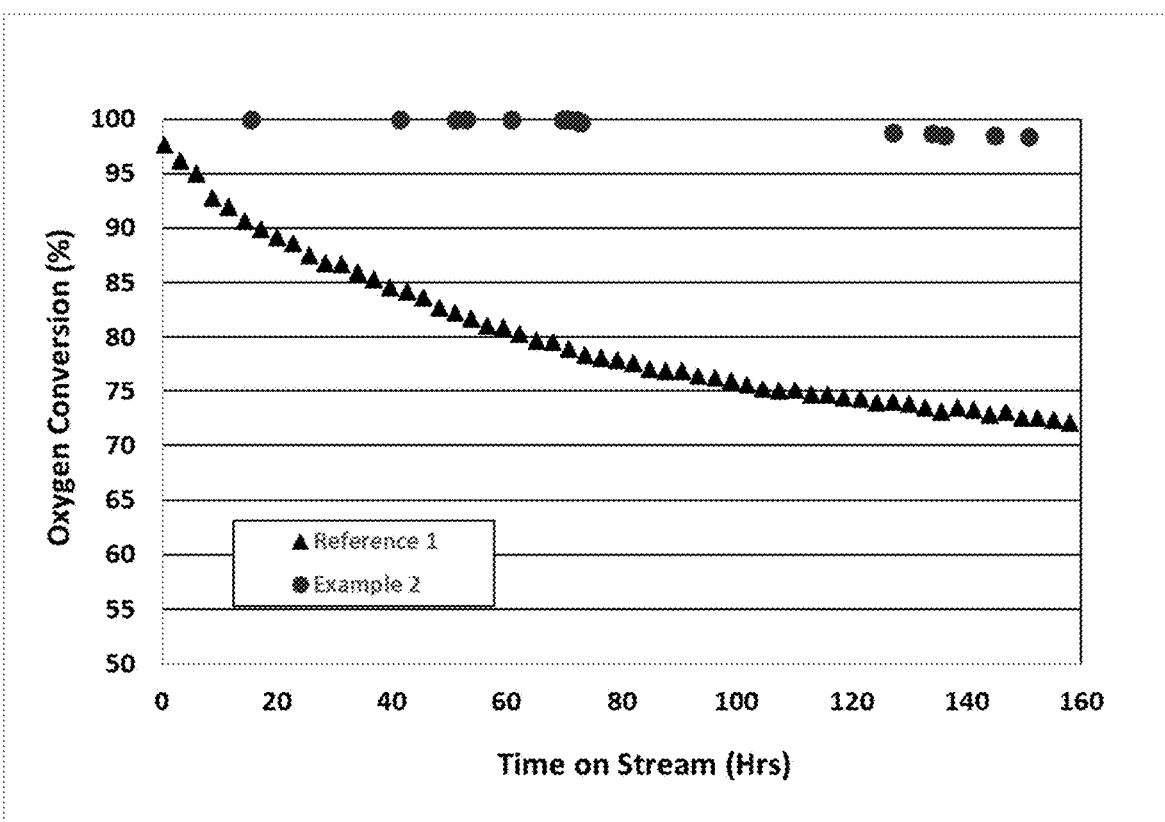
FIG. 1 is a graphical representation and comparison of oxygen conversion performance of the inventive catalyst composition of Example 2 with Reference 1 catalyst composition, over time on stream.

The invention is based, in part, on the discovery that a composition containing a catalyst, can be used for the oxidative coupling of methane with one or more benefits of having (i) high carbon efficiency and $C_{2+}$ hydrocarbon selectivity, and (ii) increased catalyst stability along with improved methane conversion and oxygen conversion. Advantageously, the catalyst composition of the present invention is formulated by calcining a metal oxide catalyst support with alkali metal promoters and mixed metal oxide precursor, containing at least one rare earth metal and at least one alkaline earth metal, enabling the formulated catalyst composition to have high carbon efficiency and increased stability under conditions suitable for OCM process.

The following includes definitions of various terms, expressions and phrases used throughout this specification.

The expressions "about" or "approximately" or "substantially" are defined as being close to as understood by one of ordinary skill in the art. In some non-limiting embodiments the terms are defined to be within 1%, preferably, within 0.1%, more preferably, within 0.01%, and most preferably, within 0.001%.

The expressions "wt. %", "vol. %", or "mol. %" refers to a weight, volume, or molar percentage of a component, respectively, based on the total weight, the total volume, or the total moles of material that includes the component. In a non-limiting example, 10 moles of a particular component present in a 100 moles of a material is 10 mol. % of component. The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The method of the invention can "comprise," "consist essentially of," or "consist of" particular ingredients, components, compositions, etc., disclosed throughout the specification. Any numerical range used through this disclosure shall include all values and ranges there between unless specified otherwise. For example, a boiling point range of 50° C. to 100° C. includes all temperatures and ranges between 50° C. and 100° C. including the temperature of 50° C. and 100° C.

The expression "$C_{2+}$ hydrocarbon" or "$C_{2+}$ hydrocarbon mixture product" as used in this disclosure means the hydrocarbon products having at least two carbon atoms including ethylene, ethane, ethyne, propene, propane, and $C_4$-$C_5$ hydrocarbons, which are produced using the inventive composition containing the catalyst of the present invention. The expression oxidative coupling of methane or "OCM" as referred or used throughout this disclosure means the oxidative coupling of methane or the reaction of methane and oxygen, for the production of $C_{2+}$ hydrocarbons from methane. The expression "redox agent" as used though out this disclosure means substances or elements which are capable of undergoing or promoting either oxidation or reduction reactions.

The expression "selectivity" to a desired product or products refers to how much desired product was formed divided by the total products formed, both desired and undesired. For purposes of the disclosure herein, the selectivity to a desired product is a percentage selectivity based on moles converted into the desired product. Further, for purposes of the disclosure herein, a $C_x$ selectivity (e.g., $C_2$ selectivity, $C_{2+}$ selectivity, etc.) can be calculated by dividing a number of moles of carbon (C) from $CH_4$ that were converted into the desired product (e.g., $C_{C2H4}$, $C_{C2H6}$, etc.) by the total number of moles of C from $CH_4$ that were converted (e.g., $C_{C2H4}$, $C_{C2H6}$, $C_{C2H2}$, $C_{C3H6}$, $C_{C3H8}$, $C_{C4S}$, $C_{CO2}$, $C_{CO}$, etc.). $C_{C2H4}$=number of moles of C from $CH_4$ that were converted into $C_2H_4$; $C_{C2H6}$=number of moles of C from $CH_4$ that were converted into $C_2H_6$; $C_{C2H2}$=number of moles of C from $CH_4$ that were converted into $C_2H_2$; $C_{C3H6}$=number of moles of C from $CH_4$ that were converted into $C_3H_6$; $C_{C3H8}$=number of moles of C from $CH_4$ that were converted into $C_3H_8$; $C_{C4S}$=number of moles of C from $CH_4$ that were converted into $C_4$ hydrocarbons ($C_4$s); $C_{CO2}$=number of moles of C from $CH_4$ that were converted into $CO_2$; $C_{CO}$=number of moles of C from $CH_4$ that were converted into CO; etc. Specifically, $C_{2+}$ hydrocarbon selectivity (e.g., selectivity to $C_{2+}$ hydrocarbons) refers to how much $C_2H_4$, $C_3H_6$, $C_2H_2$, $C_2H_6$, $C_3H_8$, $C_{5S}$ and $C_{4S}$ were formed divided by the total product formed which includes $C_2H_4$, $C_3H_6$, $C_2H_2$, $C_2H_6$, $C_3H_8$, $C_{4S}$, $C_{5S}$, $C\times_{n's}$, $CO_2$ and CO. Accordingly, a preferred way of calculating $C_{2+}$ hydrocarbon selectivity will be by using the equation (Eqn 2):

$$\left( \frac{(2C_{C2H4} + 2C_{C2H6} + 2C_{C2H2} + 2C_{C3H6} + 2C_{C3H8} + 4C_{C4s} + 5C_{C5s} + nC_{Cn's})}{(2C_{C2H4} + 2C_{C2H6} + 2C_{C2H2} + 2C_{C3H6}2C_{C3H8} + 4C_{C4s} + 5C_{C5s} + nC_{Cn's} + C_{CO2} + C_{CO})} \right) \times 100$$

Specifically, a high $C_{2+}$ hydrocarbon selectivity will signify increased formation of useful $C_{2+}$ hydrocarbon products over that of undesirable carbon oxide byproducts. The term "total product formed" used in the context of measuring selectivity includes $C_2H_4$, $C_3H_6$, $C_2H_2$, $C_2H_6$, $C_3H_8$, $C_{4S}$, $C_{5S}$, $C_{n's}$, $CO_2$ and CO.

The expression "carbon efficiency" as used throughout this disclosure means the combined selectivity of $C_{2+}$ hydrocarbon mixture products and carbon monoxide. In other words, selectivity of all carbon based products produced in an OCM reaction other than carbon dioxide.

The expression "time on stream" as used in the context of catalyst means the time period in hours which the inventive composition containing the inventive catalyst is exposed to OCM reaction conditions. The expression "carbon efficiency stability" as used throughout this disclosure means the ability of a catalyst to retain high carbon efficiency over time on stream.

The invention as described in this disclosure provides for a composition, containing a metal oxide supported catalyst comprising an alkali metal based promoter and a mixed metal component containing an alkaline earth metal and one or more rare earth metal. In some particular aspects of the invention, comprising a catalyst represented by the general formula: $[(AM_z)_{1-e}AE_aRE1_bRE2_cAT_dO_x)][(M_mO_n)_f(AM_z)_e][M_mO_n]_{1-f}$ wherein, (i) 'AM' represents an alkali metal, wherein the alkali metal is selected from the group consisting of sodium, potassium, rubidium and caesium; (ii) 'AE' represents an alkaline earth metal; (iii) 'RE1' represents a first rare earth element; (iv) 'RE2' represents a second rare earth element; (v) 'AT' represents a third rare earth element 'RE3', or a redox agent 'RX' selected from antimony, tin, nickel, chromium, molybdenum, tungsten, manganese, bismuth; wherein, 'a', 'b', 'c', 'd' and 'z' each independently represent relative molar ratio; wherein 'a' ranges from about 0.1 to about 5; 'b' ranges from about 0.01 to about 10; 'c' ranges from 0 to about 10; 'd' ranges from 0 to about 10; 'z' ranges from about 0.01 to about 10; 'x' balances the oxidation state; wherein, the first rare earth element, the second rare earth element and the third rare earth element, are different; (vi) $M_mO_n$ represents a metal oxide catalyst support which is not chemically associated with the alkali metal 'AM', wherein 'M' is a metal capable of forming an oxide reaction product on reacting with the alkali metal 'AM' under conditions of calcination, 'm' ranges from about 1 to about 5, and 'n' ranges from about 1 to about 5; and (vii) $(M_mO_n)_f(AM_z)_e$ represents an oxide reaction product produced, when a portion of the metal oxide support $(M_mO_n)$ reacts with some or all of the alkali metal 'AM', wherein 'e' and 'f' are variables that signify the partial association of the metal oxide support $M_mO_n$ with the alkali metal 'AM', with 'e' ranging from greater than zero to less than equal to 1 and 'f' ranging from greater than zero to less than 1. The variables 'e' and 'f' serve the purpose of clarifying to a skilled person that the metal oxide support and the alkali metal 'AM' will always combine chemically in a manner which is previously unseen in OCM catalysts.

As may be appreciated by a skilled person, from the range provided for the variables 'e' and 'f', it is evident that when 'e' acquires the maximum value of 1, all of the alkali metal is chemically associated with metal oxide support $M_mO_n$ while when 'e' is less than 1 but greater than zero, at least a portion of the alkali metal 'AM' is associated with the metal oxide support to form the oxide reaction product $(M_mO_n)_f(AM_z)_e$ while a part is of the alkali metal 'AM' is associated with the mixed metal component $[(AM_z)_{1-e}AE_aRE1_bRE2_cAT_dO_x)]$. On the other hand the variable 'f' is always less than 1, denoting that at least some of the metal oxide support remains free of the alkali metal 'AM'. Accordingly empirical formula, as used throughout this disclosure, and any specific formulas provided in this disclosure, should be understood to be empirical formulas representing the various elements, such as 'AM', 'RE1', 'RE2', 'RE3', 'AT' present in specific relative molar ratio and should not be understood to be the relative association of each element with the other; provided however that there will always be some alkali metal (AM) associated with metal oxide support ($M_mOn$). Without wishing to be bound by any theory, the inventors suspect that the alkali metal promoter reacts with the metal oxide support under conditions of calcinations during catalyst preparation, resulting in the formation of the temperature stable oxide reaction product represented by the empirical formula $(M_mO_n)_f(AM_z)_e$, which in turn imparts high stability to the catalyst composition by preventing the leaching of the alkali metal promoter 'AM' under high temperature conditions of OCM. For example, when the alkali metal 'AM' promoter is sodium and the metal oxide support is aluminum oxide ($Al_2O_3$), the oxide product can be a sodium aluminate compound, which has a melting point (1600° C. to 1800° C.) significantly higher than the temperature at which OCM reaction typically takes place (500° C.-1000° C.). As a consequence, the alkali metal 'AM' does not get removed or leached from the catalyst system and the catalyst is able to retain carbon efficiency stability even after substantial time on stream. This understanding is also evidenced from the XRD results shown in Table 5 of the inventive catalyst composition of Example 2, which is a catalyst composition prepared as an embodiment of the present invention, and demonstrates stability of the inventive composition even at a temperature of 850° C.

In some preferred embodiments of the invention, the alkali metal 'AM' is sodium. The term "different" as used herein means that each of the rare earth elements are different chemical elements. In some embodiments of the invention, the relative molar ratio 'z' ranges from about 0.8 to about 5, alternatively from about 1 to about 4.

In some embodiments of the invention, the alkaline earth metal 'AE' is selected from the group consisting of magnesium, calcium, strontium, barium, and combinations thereof. In some preferred embodiments of the invention, the alkaline earth metal 'AE', is strontium. In some other embodiments of the invention, the first rare earth element 'RE1', the second rare earth element 'RE2', and the third rare earth element 'RE3', are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In some aspects of the invention, the metal 'M' is any metal specie, which poses amphoteric property and can react with the alkali metal promoter to form an oxide product. In some embodiments of the invention, the metal 'M' of the metal oxide catalyst support $M_mO_n$ is selected from aluminum, zinc, tin (II), and lead (II). In some preferred embodiments of the invention, the metal oxide catalyst support $M_mO_n$ is aluminum oxide ($Al_2O_3$) with 'M' selected to be 'Al' and 'm' being 2. In some embodiments of the invention, the metal oxide support is a silicon-aluminum oxide with over 50% alumina content.

In some preferred embodiments of the invention, the alkaline earth metal 'AE' is strontium, the first rare earth element 'RE1' is lanthanum, the second rare earth element 'RE2' is neodymium, the third rare earth element 'RE3' is ytterbium and the metal oxide support is aluminum oxide ($Al_2O_3$). Without wishing to be limited by any specific theory, the incorporation of stable rare earth metal oxides imparts catalytic stability to the composition and mitigates risks of catalyst deactivation during the oxidative coupling reaction.

In some embodiments of the invention, the catalyst is represented by a general formula $Na_zSr_aLa_bNd_cYb_dO_x/Al_2O_3$, wherein 'a' ranges from about 0.1 to about 2, alternatively from about 0.2 to about 1, alternatively from about 0.3 to about 0.6; 'z' ranges from about 0.1 to about 8, alternatively from about 0.8 to about 6, alternatively from about 1 to about 5; 'b' ranges from about 0.6 to about 5, alternatively from about 0.8 to about 3, alternatively from about 1 to about 2; 'c' ranges from greater than zero to about 5, alternatively from about 0.1 to about 2, alternatively from about 0.4 to about 1; 'd' ranges from about greater than zero to about 0.4, alternatively from about 0.09 to about 0.2; and 'x' balances the oxidation state. In some preferred embodiments of the invention, the general formula is represented by the empirical formula $Na_{4.0}Sr_{0.5}La_{1.8}Nd_{0.7}Yb_{0.1}O_x/Al_2O_3$. In some preferred embodiments of the invention, the catalyst of the general formula, is represented by the empirical formula $Na_{1.0}Sr_{0.5}La_{1.8}Nd_{0.7}Yb_{0.1}O_x/Al_2O_3$. Further, without wishing to be bound by any specific theory and by way of this disclosure, it is believed that the synergistic combination of (i) metal oxide support such as alumina, with (ii) rare earth elements such as lanthanum, which promotes OCM catalyst activity, (iii) alkaline earth element such as strontium, which promotes $C_{2+}$ hydrocarbon selectivity, along with (iv) suitable proportion of alkali metal promoters, enables the composition containing the catalyst of the present invention, to demonstrate excellent carbon efficiency and improved stability. The synergistic effect of metal oxide support and the use of alkali metal promoters is evident from the example section when the results of the inventive compositions are compared with Reference 1 and Reference 2 catalyst compositions.

In some aspects of the invention, the invention provides a method for preparing the composition containing the catalyst of the present invention represented by the general formula, the method comprising: (a) impregnating an alkali metal impregnated metal oxide support with an aqueous solution of a mixed metal oxide precursor and forming a supported catalyst precursor; and (b) calcining the supported catalyst precursor at a temperature of at least 800° C., alternatively at a temperature of at least 900° C. and for at least 1 hour, alternatively for at least 5 hours, alternatively for at least 6 hours, and forming the composition.

In some preferred embodiments of the invention, the aqueous solution of the mixed metal oxide precursor, comprises at least one compound containing an alkaline earth metal 'AE' and at least one compound containing a first rare earth element 'RE1'. In some embodiments of the invention, the aqueous solution of the mixed metal oxide precursor, comprises at least one compound containing (i) an alkaline earth metal 'AE', (ii) at least one compound containing a first rare earth element 'RE1', (iii) at least one compound containing a second rare earth element 'RE2' and (iv) at least one compound containing a third rare earth element 'RE3'. In some embodiments of the invention, the aqueous solution of the mixed metal precursor can be prepared by dissolving in water at least one compound containing an alkaline earth metal 'AE' and at least one compound containing a first rare earth element 'RE1'. In some other embodiments of the invention, the aqueous solution of the mixed metal oxide precursor can be prepared by dissolving in water at least one compound containing an alkaline earth metal 'AE', at least one compound containing a first rare earth element 'RE1', at least one compound containing a second rare earth element 'RE2' and at least one compound containing a third rare earth element 'RE3'. Non-limiting examples of compounds used for preparing the mixed metal oxide precursor are nitrates, carbonates, acetates, halides, oxides, hydroxides and any combinations thereof. In some preferred embodiments of the invention, the compound chosen is a nitrate salt for each of alkaline earth metal (AE), the first rare earth element (RE1), the second rare earth element (RE2), the third rare earth element (RE3) and the redox agent. In some embodiments of the invention, the mixed metal oxide precursor is obtained by dissolving the nitrate salts of alkaline earth metal (AE), first rare earth element (RE1), second rare earth element (RE2), and third rare earth element (RE3), in water.

In some embodiments of the invention, the alkali metal impregnated metal oxide support is prepared by a method comprising the steps of: (a) impregnating a metal oxide support with a solution comprising an alkali metal compound and forming an alkali metal impregnated support precursor; and (b) calcining the alkali metal impregnated metal oxide support precursor at a temperature of at least 800° C., alternatively at a temperature of at least 900° C. and for at least 1 hour, alternatively for at least 5 hours, alternatively for at least 6 hours, and forming the alkali metal impregnated metal oxide support. In some preferred embodiments of the invention, the alkali metal compound is an alkali metal salt. Non limiting examples of alkali metal salt includes alkali metal nitrates, alkali metal chlorides, alkali metal halides, alkali metal carbonates, and alkali metal oxides. In some preferred embodiments of the invention, the alkali metal compound is a sodium salt. In some preferred embodiments of the invention, the alkali metal compound is sodium nitrate.

In some aspects of the invention, a composition comprising a $C_{2+}$ hydrocarbon mixture product is formed using the composition of the present invention containing the catalyst of the present invention. In some aspects of the invention, $C_{2+}$ hydrocarbon mixture product comprises ethylene, ethane, ethyne, propene, propane, $C_4$-$C_5$ hydrocarbons, carbon dioxide, carbon monoxide and combinations thereof. In some aspects of the invention, the invention describes a process for preparing a $C_{2+}$ hydrocarbon mixture product comprising (a) introducing a feed mixture comprising methane and oxygen in a reactor containing the composition comprising the catalyst of the present invention represented by the general formula; (b) subjecting the feed mixture to a methane coupling reaction under conditions suitable to produce the $C_{2+}$ hydrocarbon mixture product; and (c) recovering the $C_{2+}$ hydrocarbon mixture product after removing unconverted methane from the $C_{2+}$ hydrocarbon mixture product. In some aspects of the invention, unconverted methane produced during the reaction, is removed from the $C_{2+}$ hydrocarbon mixture product. In some embodiments of the invention, the removal of unconverted methane from the $C_{2+}$ hydrocarbon mixture product is effected using a distillation column. In some embodiments of the invention, the distillation column is a cryogenic distillation column.

Methane coupling reaction under conditions suitable to produce $C_{2+}$ hydrocarbon mixture product include appropriate temperature conditions, pressure conditions to effect the coupling reaction. In some embodiments of the invention, the feed mixture comprising methane and oxygen may be preheated to a temperature ranging from about 200° C. to about 550° C., prior to introducing the feed mixture in the reactor for methane coupling. The reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In one preferred aspect of the invention, a 2.3 mm ID quartz tube reactor is used for the purposes of reacting oxygen with methane under conditions sufficient to effect the oxidative coupling of methane. In some aspects of the invention, the reactor can comprise an adiabatic reactor. In some aspects of the invention, the $C_{2+}$ hydrocarbon mixture product is produced at a reactor temperature ranging from about 500° C. to about 1000° C., alternatively from about 600° C. to about 950° C., alternatively from about 700° C. to about 900° C.

In some aspects of the invention, the reactor can comprise a catalyst bed comprising the composition capable of catalyzing the oxidative coupling of methane reaction. In some embodiments of the invention, the feed mixture has a methane to oxygen molar ratio ranging from about 2:1 to about 15:1, alternatively from about 4:1 to about 10:1, alternatively from about 5:1 to about 8:1. In some embodiments of the invention, the pressure in the reactor is maintained at a pressure sufficient to effect oxidative coupling of methane. The pressure may be maintained at a range of about 14.7 psi (ambient atmospheric pressure) to about 500 psi, alternatively at a range of about 14.7 psi (ambient atmospheric pressure) to about 200 psi, alternatively at a range of about 14.7 psi (ambient atmospheric pressure) to about 150 psi. In some embodiments of the invention, the feed mixture is introduced into the reactor at a gas hourly space velocity (GHSV) ranging from about 500 $h_{-1}$ to about 1,000,000 $h^{-1}$, alternatively from about 1,000 $h^{-1}$ to about 500,000 $h^{-1}$, alternatively from about 5,000 $h^{-1}$ to about 400,000 $h_{-1}$.

In some aspects of the invention, the composition containing the catalyst of the present invention, has a carbon efficiency ranging from about 87% to about 95%, alternatively from about 87.5% to about 94%, alternatively from about 88% to about 93%, of total product formed, when the composition is used in a process for producing $C_{2+}$ hydrocarbon from methane and oxygen. The expression "carbon efficiency" as has been defined earlier, is associated with selectivity towards $C_{2+}$ hydrocarbons and carbon monoxide (CO). A higher carbon efficiency for an OCM process is particularly beneficial as it results in higher selectivity towards the more commercially valuable $C_{2+}$ hydrocarbons, while reducing selectivity towards waste by-product carbon dioxide. The expression "total product formed" used in the context of measuring selectivity includes the products formed of $C_2H_4$, $C_3H_6$, $C_2H_2$, $C_2H_6$, $C_3H_8$, $C_{4S}$, $C_{5S}$, $C_{n's}$, $CO_2$ and CO. In some aspects of the invention, the composition containing the catalyst of the present invention, has a carbon dioxide ($CO_2$) selectivity ranging from about 5% to about to about 13%, alternatively from about 7% to about 12.5%, or alternatively from about 9% to about 12%, of the total product formed, when the composition is used in a process for producing $C_{2+}$ hydrocarbon mixture product from methane and oxygen. The improved carbon efficiency stability with increase time on stream is evident from the results of Example 1 and Example 2 and particularly demonstrated in FIG. 4.

The carbon efficiency can be measured over a range of temperature ranging from about 450° C. to about 850° C. The catalyst performance in terms of the carbon efficiency in the initial period on stream, for example for a time period less than 10 hours, may be noted and subsequently the catalyst performance over a longer period on stream may be noted. The improved carbon efficiency and stability exhibited by the inventive catalyst composition, results in lowering of the overall heat produced during the coupling reaction, improving catalyst performance and aiding in controlling reactor operations. In various aspects of the invention, the composition containing the inventive catalyst demonstrates suitable balance of methane conversion, oxygen conversion and carbon efficiency. The balance between methane/oxygen conversion and carbon efficiency is particularly beneficial as this signifies a balance between selectivity and catalytic reactivity, which are generally of opposite attributes.

The methane and oxygen conversion can be measured by using methane or oxygen concentration using a gas chromatograph. The methane conversion can be determined using the equation: ($CH_4$ (inlet)—$CH_4$ (outlet)/$CH_4$ (inlet))×100, (Eqn 3), where $CH_4$ (inlet) is the concentration of methane in terms of moles, at the inlet of the reactor and $CH_4$ (outlet) is the concentration of methane, in terms of moles, at the outlet. For the purposes of this invention, methane conversion can be measured by comparing the methane concentration at the outlet and the inlet of an oxidative coupling of methane reactor, such a reactor being a 2.3 mm ID quartz tube reactor having a feed mixture flow rate adjusted from about 40 or 160 sccm and a catalyst loading of 20 mg. Similarly, oxygen conversion can be measured by using the equation: ($O_2$ (inlet)—$O_2$ (outlet)/$O_2$ (inlet))×100, (Eqn 4), where $O_2$ (inlet) is the concentration of oxygen in terms of moles, at the inlet of the reactor and $O2$ (outlet) is the concentration of oxygen, in terms of moles, at the outlet. For the purposes of this invention, oxygen conversion can be measured by comparing the oxygen concentration at the outlet and the inlet of an oxidative coupling of methane reactor, such a reactor being a 2.3 mm ID quartz tube reactor having a feed mixture flow rate adjusted from about 40 or 160 sccm and a catalyst loading of 20 mg. Accordingly, the invention includes various embodiments related to catalyst compositions that exhibit one or more benefits of having (i) high carbon efficiency and $C_{2+}$ hydrocarbon selectivity, (ii) increased catalyst stability with high carbon efficiency along with improved methane and oxygen conversion.

Specific examples demonstrating some of the embodiments of the invention are included below. The examples are for illustrative purposes only and are not intended to limit the invention. It should be understood that the embodiments and the aspects disclosed herein are not mutually exclusive and such aspects and embodiments can be combined in any way. Those of ordinary skill in the art will readily recognize parameters that can be changed or modified to yield essentially the same results.

EXAMPLES

Example 1

Catalyst composition having the empirical formula ($Na_{4.0}Sr_{0.5}La_{1.8}Nd_{0.7}Yb_{0.1}O_x/Al_2O_3$)

Purpose: Example 1, as an embodiment of the present invention, demonstrates the preparation and use of a composition comprising alumina supported, alkali metal promoted catalyst, having the empirical formula ($Na_{4.0}Sr_{0.5}La_{1.8}Nd_{0.7}Yb_{0.1}O_x/Al_2O_3$). It should be understood that in this Example 1 and in all Examples wherein actual metals are shown rather than the variable symbols AM, AE, RE1, RE2, and AT, such formulas are empirical, provided however, that the partitioning of the alkali metal between the support $M_mO_n$ and the other components is still present as expressed in the general formula. In this way, such empirical formulas fall within the general formula and although the $Al_2O_3$ is shown alone, there is always some alkali metal associated with it. The performance of the inventive catalyst composition of Example 1 in terms of stability and carbon efficiency is compared with Reference 2 catalyst composition.

Materials: The following materials are procured and used for the synthesis of the composition.

TABLE 1

| Inventive catalyst composition ($Na_{4.0}Sr_{0.5}La_{1.8}Nd_{0.7}Yb_{0.1}O_x/Al_2O_3$) | | | | |
| --- | --- | --- | --- | --- |
| Catalyst composition: $AM_zAE_aRE1_bRE2_cAT_dO_x/M_mO_n$ | Element/ Compound used | Relative molar ratio | Precursor Material | Supplier |
| AM | Sodium (Na) | z = 4.0 | Sodium Nitrate $Na(NO_3)$ | Sigma-Aldrich |
| AE | Strontium (Sr) | a = 0.5 | Strontium Nitrate: $Sr(NO_3)_2$ | Sigma-Aldrich |
| RE1 | Lanthanum (La) | b = 1.8 | Lanthanum Nitrate $La(NO_3)_3·6H_2O$ | Sigma-Aldrich |
| RE2 | Neodymium (Nd) | c = 0.7 | Neodymium Nitrate: $Nd(NO_3)_3·6H_2O$ | Sigma-Aldrich |
| AT = RE3 | Ytterbium (Yb) | d = 0.1 | Ytterbium Nitrate $Yb(NO_3)_3·5H_2O$ | Sigma-Aldrich |
| $M_mO_n$ | Alumina ($Al_2O_3$) | | SA5162 Alumina | Saint-Gobain |

Method for preparing the composition containing the inventive catalyst of Example 1 ($Na_{4.0}Sr_{0.5}La_{1.8}Nd_{0.7}Yb_{0.1}O_x/Al_2O_3$): The composition containing the catalyst of Example 1, was prepared by a general method of (a) impregnating an alkali metal impregnated metal oxide support with an aqueous solution of a mixed metal oxide precursor and forming a supported catalyst precursor, and (ii) calcining the supported catalyst precursor at a temperature of at least 800° C. and for at least 1 hour, preferably at least 5 hours, preferably at least 6 hours, and forming the composition containing the catalyst of Example 1.

More specifically, the method included the step of, first obtaining the aqueous solution of the mixed metal oxide precursor by dissolving 1.66 g of strontium nitrate ($Sr(NO_3)_2$), 12.25 g of lanthanum nitrate ($La(NO_3)_3.6H_2O$), 4.82 g of neodymium nitrate ($Nd(NO_3)_3.6H_2O$) and 0.63 g of ytterbium nitrate ($Yb(NO_3)_3.6H_2O$) in 18 mL of distilled water. Separately, the alkali metal impregnated metal oxide support precursor was prepared by dissolving 9.44 g of an alkali metal compound in the form of sodium nitrate ($Na(NO_3)$) in 10 mL of distilled water and subsequently the aqueous solution so formed was impregnated in 10.0 g of 20-60 mesh $Al_2O_3$ support (SA5162 from Saint-Gobain). The alkali metal impregnated metal oxide support precursor was thereafter dried overnight at 120° C. and then calcined at 900° C. for 6 hours to obtain the alkali metal impregnated metal oxide support. The alkali metal impregnated metal oxide support was impregnated with the aqueous solution of the mixed metal oxide precursor that was obtained and subsequently dried overnight at 120° C. and followed by calcination at 900° C. for 6 hours, to obtain the inventive composition of Example 1.

Process for producing $C_{2+}$ hydrocarbon mixture product using the composition of Example 1: The composition containing the inventive catalyst of Example 1, was thereafter used for producing $C_{2+}$ hydrocarbon mixture product using the process comprising (a) introducing a feed mixture comprising methane and oxygen in a reactor containing the inventive composition of Example 1; (b) subjecting the feed mixture to a methane coupling reaction under conditions suitable to produce the $C_{2+}$ hydrocarbon mixture product; and (c) recovering the $C_{2+}$ hydrocarbon mixture product after removing unconverted methane from the $C_{2+}$ hydrocarbon mixture product. More particularly, the composition containing the catalyst obtained from Example 1, was placed in a 2.3 mm ID quartz tube, and was contacted with a feed mixture containing methane and oxygen. The ratio of methane to oxygen was adjusted to a molar ratio of 7.4:1 and the feed mixture flow rate was adjusted from 40 sccm. The catalyst loading in the reactor was 20 mg. The reactor temperature was gradually changed from 450° C. to 850° C. and the catalyst performance was recorded. The highest selectivity and carbon efficiency data obtained are used for comparison. The $C_{2+}$ hydrocarbon mixture product so obtained was analyzed using online Gas Chromatograph, Agilent 7890 GC, having a thermal conductivity detector (TCD) and a flame ionization detector (FID). The performance of the inventive catalyst composition of Example 1, in terms of carbon efficiency was measured at various time on stream, which the inventive catalyst composition of Example 1 was exposed to.

Results: The catalyst performance obtained in the initial period of time on stream for a time period less than 10 hours, is tabulated below. Carbon efficiency was determined by combining the selectivity of $C_{2+}$ hydrocarbon products and carbon monoxide. Selectivity was determined using Eqn 2 and the molar concentration of various species was measured using the gas chromatograph.

TABLE 2

Carbon efficiency and $CO_2$ selectivity
($Na_{4.0}Sr_{0.5}La_{1.8}Nd_{0.7}Yb_{0.1}O_x/Al_2O_3$)

| | Highest Carbon Efficiency (%) at time on stream less than 10 hours (initial period) | Lowest Carbon dioxide selectivity (%) at time on stream less 10 hours (initial period) |
|---|---|---|
| Inventive catalyst composition Example 1 | 88.0 | 12.0 |

Figure 4:
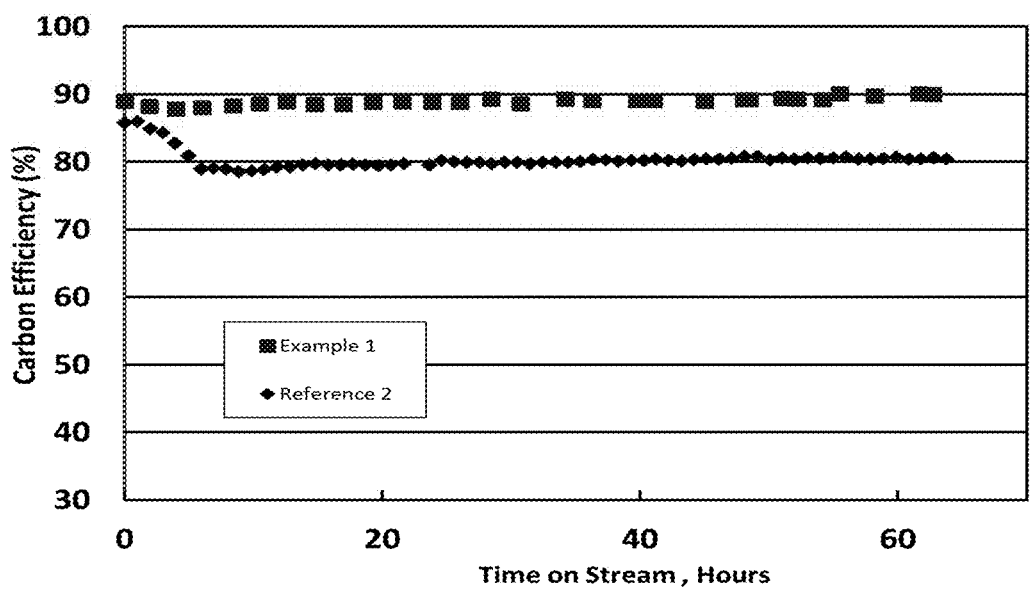
FIG. 4 is a graphical representation and comparison of carbon efficiency performance of the inventive catalyst composition of Example 1 with Reference 2 catalyst composition, over time on stream.

As shown in FIG. 4, the inventive composition of Example 1 retains high carbon efficiency even with increased time on stream. The deterioration in carbon efficiency is not significant when compared with that of Reference 2 catalyst.

Example 2

Catalyst composition having the formula ($Na_{1.0}Sr_{0.5}La_{1.8}Nd_{0.7}Yb_{0.1}O_x/Al_2O_3$).

Purpose: Example 2 demonstrates the preparation and use of a composition comprising alumina supported, alkali metal promoted catalyst, having the formula ($Na_{1.0}Sr_{0.5}La_{1.8}Nd_{0.7}Yb_{0.1}O_x/Al_2O_3$). The composition of Example 2, has a lower content of alkali metal compared to the composition of Example 1.

Materials: The following materials are procured and used for the synthesis of the composition.

TABLE 3

Inventive catalyst composition ($Na_{1.0}Sr_{0.5}La_{1.8}Nd_{0.7}Yb_{0.1}O_x/Al_2O_3$)

| Catalyst composition: $AM_zAE_aRE1_bRE2_cAT_dO_x$/ $M_mO_n$ | Element/ Compound used | Relative molar ratio | Precursor Material | Supplier |
|---|---|---|---|---|
| AM | Sodium (Na) | z = 1.0 | Sodium Nitrate $Na(NO_3)$ | Sigma-Aldrich |
| AE | Strontium (Sr) | a = 0.5 | Strontium Nitrate: $Sr(NO_3)_2$ | Sigma-Aldrich |
| RE1 | Lanthanum (La) | b = 1.8 | Lanthanum Nitrate $La(NO_3)_3 \cdot 6H_2O$ | Sigma-Aldrich |

TABLE 3-continued

Inventive catalyst composition ($Na_{1.0}Sr_{0.5}La_{1.8}Nd_{0.7}Yb_{0.1}O_x/Al_2O_3$)

| Catalyst composition: $AM_zAE_aRE1_bRE2_cAT_dO_x/$ $M_mO_n$ | Element/ Compound used | Relative molar ratio | Precursor Material | Supplier |
|---|---|---|---|---|
| RE2 | Neodymium (Nd) | c = 0.7 | Neodymium Nitrate: $Nd(NO_3)_3 \cdot 6H_2O$ | Sigma-Aldrich |
| AT = RE3 | Ytterbium (Yb) | d = 0.1 | Ytterbium Nitrate $Yb(NO_3)_3 \cdot 5H_2O$ | Sigma-Aldrich |
| $M_mO_n$ | Alumina ($Al_2O_3$) | | SA5162 Alumina | Saint-Gobain |

Method for preparing the composition containing the inventive catalyst of Example 2 ($Na_{1.0}Sr_{0.5}La_{1.8}Nd_{0.7}Yb_{0.1}O_x/Al_2O_3$): The inventive catalyst composition of Example 2 was prepared in the same manner as was described under Example 1 save and except for using a lower proportion of alkali metal sodium with 2.36 g of sodium nitrate being used for the preparation.

Process for producing $C_{2+}$ hydrocarbon mixture product using the composition of Example 2: The composition containing the inventive catalyst of Example 2, was thereafter used for producing $C_{2+}$ hydrocarbon mixture product using the process conditions and methodology identical to that described in Example 1.

Results: The catalyst performance obtained using the catalyst composition of Example 2, is tabulated below.

TABLE 4

Carbon efficiency and $CO_2$ selectivity ($Na_{1.0}Sr_{0.5}La_{1.8}Nd_{0.7}Yb_{0.1}O_x/Al_2O_3$)

| | Highest Carbon Efficiency (%) at time on stream less than 10 hours (initial period) | Lowest Carbon dioxide selectivity (%) at time on stream less 10 hours (initial period) |
|---|---|---|
| Inventive catalyst composition Example 2 | 87.7 | 12.3 |

The presence of the oxide reaction product of sodium aluminate is evidenced from qualitative assessment data derived from hot stage XRD pattern and shown in Table 5, which denotes stability of the Example 2 catalyst composition even at temperatures as high as 850° C.

TABLE 5

Stability of NaAlO2 phase in Example 2 catalyst

| Temperature of XRD cell (° C.) | Duration at the set temperature | Qualitative assessment of sodium aluminate ($NaAlO_2$) phase content as wt. % of catalyst composition |
|---|---|---|
| 850 | 10 min. | 45% |
| 850 | 3 hours | 45% |
| 850 | 5 hours | 45% |
| 850 | 7 hours | 46% |

The presence of sodium aluminate as determined by way of XRD study is a qualitative assessment of the amount of sodium aluminate that is present in the composition. However, the presence of sodium aluminate in the catalyst composition as observed under Table 5, impart previously unseen stability in terms of oxygen and methane conversion as evidenced from FIG. 1 and FIG. 2. As shown in these figures the oxygen and methane conversion remains steady even with prolonged time on stream indicating suitability of Example 2 catalyst for oxidative coupling of methane (OCM).

Example 3

Catalyst composition having the empirical formula ($Na_{1.0}Sr_{0.5}La_{1.8}Nd_{0.7}Yb_{0.1}O_x/Al_2O_3$).

Purpose: Example 3 demonstrates the application of the inventive composition prepared under Example 2 at four times higher flow rate severity compared to Example 2.

Process for producing $C_{2+}$ hydrocarbon mixture product using the composition of Example 3: The composition obtained from the practice of Example 2, was thereafter used for producing $C_{2+}$ hydrocarbon mixture product using the process conditions and methods identical to that described in Example 1 and Example 2, save and except for a higher flow rate severity of 160 sccm (four times than that used for the purposes of Example 1 and Example 2). The performance of the inventive catalyst composition of Example 3, in terms of carbon efficiency was measured at the initial stage of time on stream of less than 10 hours.

Results: The catalyst performance obtained using the catalyst composition of Example 3, is tabulated below.

TABLE 6

Carbon efficiency and CO$_2$ selectivity
(Na$_{1.0}$Sr$_{0.5}$La$_{1.8}$Nd$_{0.7}$Yb$_{0.1}$O$_x$/Al$_2$O$_3$)

| | Highest Carbon Efficiency (%) at time on stream less than 10 hours (initial period) | Lowest Carbon dioxide selectivity (%) at time on stream less 10 hours (initial period) |
|---|---|---|
| Inventive catalyst composition Example 3 | 89.1 | 10.9 |

From the results obtained from Table 6, it may be concluded that the inventive composition of Example 3, is able to demonstrate high carbon efficiency and low carbon dioxide selectivity even under higher flow rate severity conditions thereby enabling a skilled person to use the inventive catalyst under a broad range of operating conditions with high carbon efficiency.

REFERENCE 1 CATALYST (COMPARATIVE)

Catalyst composition having the formula (Mn—Na$_2$WO$_4$/SiO$_2$)

Purpose: Reference 1 catalyst composition is taken as a control and comprises a catalyst having the formula (Mn—Na$_2$WO$_4$/SiO$_2$). The Reference 1 catalyst is described in the published literature (Arndt et al. Applied Catalysis A Published Mar. 6, 2012: General 425-426 (2012) 53-61 Mn—Na2WO4/SiO2: as catalyst for the oxidative coupling of methane. What is really known). Reference 1 catalyst is a widely studied OCM catalyst with a proven track record in terms of selectivity and carbon efficiency. Reference 1 catalyst composition contains sodium promoter and a silica based support and is particularly a suitable comparative catalyst composition, as the technical effects of incorporating a support of the type contemplated under the present invention with an alkali metal promoter can be evaluated.

Preparation: The catalyst was prepared using the following procedure using the incipient wetness method: A silica gel (18.6 g, Davisil® Grade 646) was provided after drying overnight. Mn(NO$_3$)$_2$.4H$_2$O (1.73 g) was dissolved in deionized water (18.5 ml) and then added dropwise onto a silica gel material (18.6 g Davisil® Grade 646), and the resulting manganese impregnated silica material was subsequently dried overnight. Na$_2$WO$_4$.4H$_2$O (1.13 g) was dissolved in deionized water (18.5 ml) and the solution obtained was added onto the dried manganese impregnated silica material obtained from the above step. The resulting material was dried overnight at a temperature of 125° C. and subsequently calcined at a temperature of 800° C. for 6 hours under airflow to obtain the Reference 1 catalyst Mn—Na$_2$WO$_4$/SiO$_2$. The Reference 1 composition was then crushed and tested for its performance Process for producing C$_{2+}$ hydrocarbon mixture product using the composition of Reference 1: The Reference 1 catalyst as obtained was used for producing C$_{2+}$ hydrocarbon mixture product using the process and operating parameters as described under Example 1, save and except for a higher catalyst loading of about 100 mg instead of 20 mg that was used for the purposes of Example 1 and Example 2. The Reference 1 catalyst with a five times higher load was used so as to offset the low reactivity of the Reference 1 catalyst and obtain meaningful data for suitable comparison.

Results: The carbon efficiency results of Reference 1 catalyst are provided in the table below in comparison with Example 1-3 of the inventive composition:

TABLE 7

Carbon efficiency and CO$_2$ selectivity

| | Highest Carbon Efficiency (%) at time on stream less than 10 hours (initial period) | Lowest Carbon dioxide selectivity (%) at time on stream less 10 hours (initial period) |
|---|---|---|
| Comparative Reference 1 catalyst | 90.3 | 9.7 |
| Inventive catalyst composition Example 1 | 88.0 | 12.0 |
| Inventive catalyst composition Example 2 | 87.7 | 12.3 |
| Inventive catalyst composition Example 3 | 89.1 | 10.1 |

Figure 2:
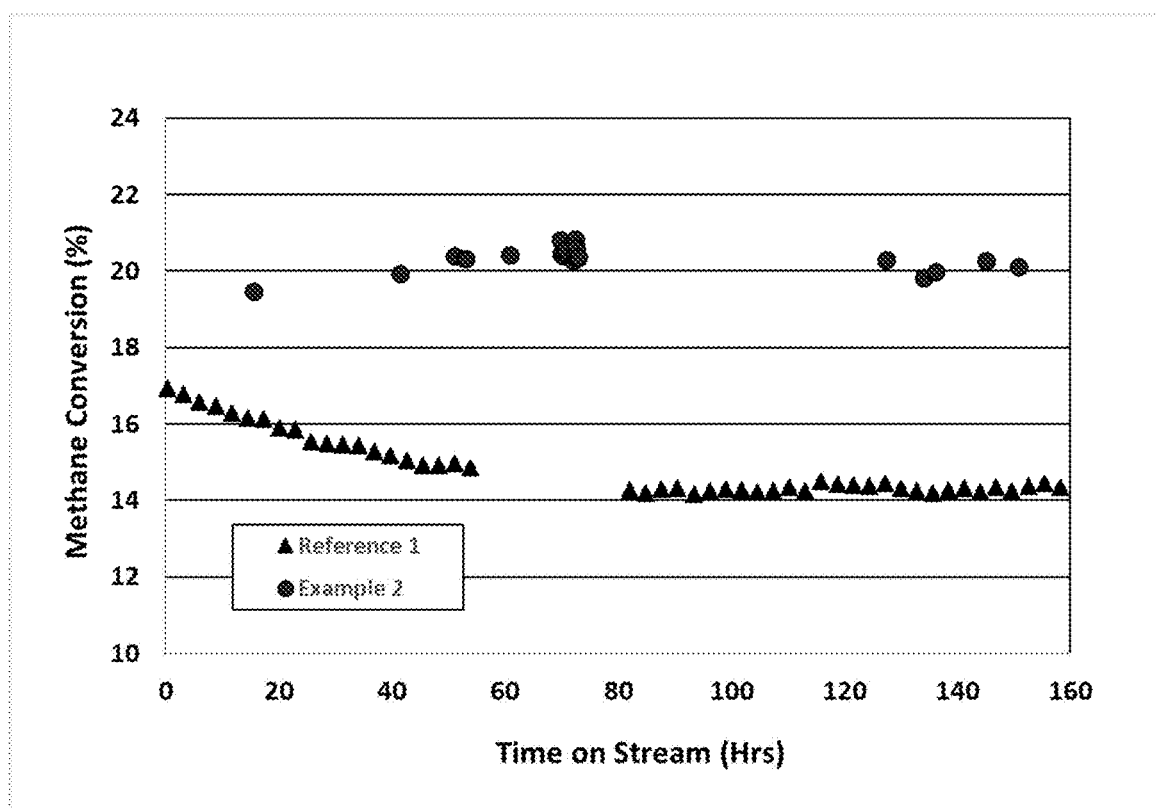
FIG. 2 is a graphical representation and comparison of methane conversion performance of the inventive catalyst composition of Example 2 with Reference 1 catalyst composition, over time on stream.

Although the results from Table 7, indicate that the composition of Reference 1 has a higher overall carbon efficiency and lower carbon dioxide selectivity, the catalyst loading of Reference 1 catalyst was 5 times higher (100 mg vs 20 mg) than the inventive compositions to obtain nearly similar levels of carbon efficiency. Thus, the inventive catalyst compositions (Example 1-3) prepared as embodiments of the present invention, are more effective for OCM process than that of Reference 1. From FIG. 1 it may be concluded that the oxygen conversion of Reference 1 catalyst composition, when compared to the Example 2 catalyst composition, showed rapid deterioration in oxygen conversion property over time on stream indicating rapid loss of catalyst activity. With rapid loss of catalyst activity of Reference 1 catalyst composition over time on stream, its methane conversion also drops rapidly with time on stream as shown in FIG. 2.

Figure 3:
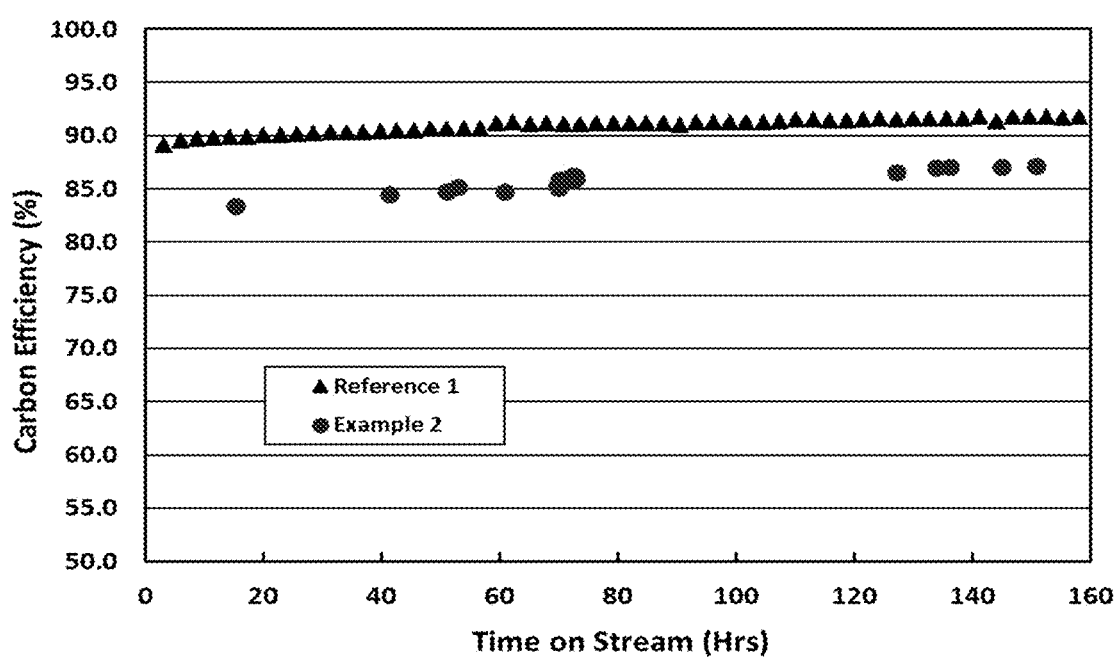
FIG. 3 is a graphical representation and comparison of carbon efficiency performance of the inventive catalyst composition of Example 2 with Reference 1 catalyst composition, over time on stream.

On the contrary, Example 2 catalyst composition demonstrated stable oxygen and methane conversions even with ⅕ of catalyst loading. This comparison clearly indicates that Example 2 is much better suited for long term commercial application for OCM than Reference 1 catalyst composition, even though, the carbon efficiency of Reference 1 catalyst composition is marginally higher than Example 2 catalyst as shown in FIG. 3. Without wishing to be bound by any specific theory, it is suspected that the presence of metal oxide such as alumina, which is capable of reacting with alkali metal promoters to form aluminates, results in previously unseen benefits of improved catalyst stability particularly improved methane and oxygen conversion. Therefore, it may be concluded, that the mere incorporation of a typical oxide support such as silica, in an OCM catalyst system, may not necessarily impart improved stability and carbon efficiency to an OCM catalyst.

REFERENCE 2 CATALYST (COMPARATIVE)

Catalyst composition having the formula $(Na_{1.0}Sr_{1.0}La_{0.5}Nd_{0.1}Er_{0.3}O_x)$ Purpose: Reference 2 catalyst composition is taken as a control and comprises a catalyst having an alkali metal promoter. Reference 2 catalyst has the formula $(Na_{1.0}Sr_{1.0}La_{0.5}Nd_{0.1}Er_{0.3}O_x)$. The key difference in features between the composition of Reference 2 catalyst and that of the catalyst composition obtained from Example 1 or Example 2, is the absence of metal oxide support in Reference 2 catalyst. Reference 2 catalyst composition is therefore a suitable comparative to the composition of the present invention, as it provides opportunity to evaluate the synergistic combination of alkali metal promoters and metal oxide support.

Preparation: The following steps were followed for the synthesis of Reference 2 catalyst composition: 1.7 g of sodium nitrate $(Na(NO_3))$ 4.23 g of strontium nitrate $(Sr(NO_3)_2)$, 4.33 g of lanthanum nitrate $(La(NO_3)_3 \cdot 6H_2O)$, 0.88 g of neodymium nitrate $(Nd(NO_3)_3 \cdot 6H_2O)$, 2.66 g of erbium nitrate $(Er(NO_3)_3 \cdot 6H_2O)$ were mixed and dissolved in 50 ml of distilled water to form a solution. The solution was subsequently dried overnight at a temperature of 120° C. followed by calcination at 900° C. for 6 hours to obtain the control composition of Reference 2 catalyst composition. The Reference 2 catalyst composition was subsequently crushed and tested for its performance.

Process for producing $C_{2+}$ hydrocarbon mixture product using the composition of Reference 2: The Reference 2 catalyst as obtained above was used for producing $C_{2+}$ hydrocarbon mixture product using the process and operating parameters as described under Example 1. The results for carbon efficiency stability was subsequently compared with the inventive composition of Example 1 (having a lower alkali metal content), the results of which is shown under FIG. 4.

Results: The carbon efficiency results of Reference 2 catalyst composition is provided in the table below, in comparison with Example 1-3 of the inventive compositions:

TABLE 8

Carbon efficiency and $CO_2$ selectivity $(Na_{1.0}Sr_{1.0}La_{0.5}Nd_{0.1}Er_{0.3}O_x)$

|  | Highest Carbon Efficiency (%) at time on stream less than 10 hours (initial period) | Lowest Carbon dioxide selectivity (%) at time on stream less 10 hours (initial period) |
|---|---|---|
| Comparative Reference 2 catalyst | 86.0 | 14.0 |
| Inventive catalyst composition Example 1 | 88.0 | 12.0 |
| Inventive catalyst composition Example 2 | 87.7 | 12.3 |

TABLE 8-continued

Carbon efficiency and $CO_2$ selectivity $(Na_{1.0}Sr_{1.0}La_{0.5}Nd_{0.1}Er_{0.3}O_x)$

|  | Highest Carbon Efficiency (%) at time on stream less than 10 hours (initial period) | Lowest Carbon dioxide selectivity (%) at time on stream less 10 hours (initial period) |
|---|---|---|
| Inventive catalyst composition Example 3 | 89.1 | 10.1 |

The results from Table 8, indicate that the composition of Reference 2 has a marginally lower carbon efficiency than the inventive compositions of Example 1 and Example 2. However, as illustrated under FIG. 4, the carbon efficiency of the Reference 2 catalyst composition rapidly declines with increasing time on stream indicating that the Reference 2 catalyst has a significantly lower stability under OCM conditions than that of the inventive catalyst composition of Example 1. Without wishing to be bound by any specific theory, the inventors suspect that the presence of metal oxide support such as alumina, which is capable of partially reacting with alkali metal promoters to form aluminates, imparts improved stability and carbon efficiency to the Example 1 catalyst composition.

REFERENCE 3 CATALYST (COMPARATIVE)

Catalyst composition having the formula $(Sr_{0.5}La_{1.8}Nd_{0.7}Yb_{0.1}O_x/Al_2O_3)$ Purpose: Reference 3 catalyst composition is taken as a control and comprises a catalyst having an alumina support but does not contain any alkali metal promoter. Reference 3 catalyst has the formula $(Sr_{0.5}La_{1.8}Nd_{0.7}Yb_{0.1}O_x/Al_2O_3)$. The key difference between the composition of Reference 3 catalyst and that of the inventive catalyst composition of Example 1 or Example 2, is the absence of alkali metal promoter in Reference 3 catalyst composition. Reference 3 catalyst composition is therefore a suitable comparative to the present invention as it provides opportunity to evaluate the synergistic combination of alkali metal promoters and metal oxide support as contemplated in the present invention.

Preparation: The following steps were followed for the synthesis of Reference 3 catalyst composition: Alumina obtained from SAINT-GOBAIN SA5162 was used. An aqueous solution of mixed metal oxide precursor was prepared by dissolving 1.66 g of strontium nitrate $(Sr(NO_3)_2)$, 12.25 g of lanthanum nitrate $(La(NO_3)_3 \cdot 6H_2O)$, 4.82 g of neodymium nitrate $(Nd(NO_3)_3 \cdot 6H_2O)$ and 0.63 g of ytterbium nitrate $(Yb(NO_3)_3 \cdot 6H_2O)$ in 18 mL of distilled water. The aqueous solution was thereafter impregnated on the alumina support. The material so obtained was subsequently dried overnight at a temperature of 120° C. followed by calcination at 900° C. for 6 hours. The Reference 3 catalyst composition was then crushed and tested for its performance.

Process for producing $C_{2+}$ hydrocarbon mixture product using the composition of Reference 3: The Reference 3 catalyst as obtained above was used for producing $C_{2+}$ hydrocarbon mixture product using the process and operating parameters as described under Example 1.

Results: The carbon efficiency results of Reference 3 catalyst composition is provided in the table below, in comparison with Example 1-3 of the inventive compositions:

TABLE 9

Carbon efficiency and CO$_2$ selectivity
($Sr_{0.5}La_{1.8}Nd_{0.7}Yb_{0.1}O_x/Al_2O_3$)

|  | Highest Carbon Efficiency (%) at time on stream less than 10 hours (initial period) | Lowest Carbon dioxide selectivity (%) at time on stream less 10 hours (initial period) |
| --- | --- | --- |
| Comparative Reference 3 catalyst | 83.0 | 17.0 |
| Inventive composition Example 1 | 88.0 | 12.0 |
| Inventive composition Example 2 | 87.7 | 12.3 |
| Inventive composition Example 3 | 89.1 | 10.1 |

The results from Table 9, indicate that Reference 3 catalyst composition has a significantly lower carbon efficiency than the inventive compositions of Example 1 and Example 2, even at the initial period on stream (<10 hours). As evidenced from the results provided in Reference 2 and Reference 3, the inventors suspect that the synergistic combination of alkali metal promoters with metal oxide support impart improved carbon efficiency and stability, which is previously unseen in OCM catalyst systems.

Summary—From the example section summarized under Table 10 below, it is evident that in the initial period on stream, the catalyst compositions, which have alkali metals such sodium in its composition demonstrate improved carbon efficiency and reduced selectivity towards carbon dioxide. This will be particularly evident for a skilled person, while noting that the carbon efficiency of Reference 3 catalyst is significantly lower than the other catalyst compositions which has sodium in its composition. However, the mere presence of sodium is not sufficient to ensure improved stability of catalyst over a longer period on stream as evidenced from the results shown in FIG. 4 where Reference 2 catalyst composition demonstrates reduced carbon efficiency over longer time on stream with rapid loss in catalyst performance. On the other hand, the inventive catalyst composition demonstrates steady catalyst performance over prolonged period of time on stream. Similarly, from the results illustrated in FIG. 1 and FIG. 2, when read with the results illustrated in FIG. 3, it may be appreciated by a skilled person, that although Reference 1 catalyst composition, which has a sodium tungstate component and a silica support, provides excellent carbon efficiency in the initial period on stream, which may even be marginally better than the inventive catalyst of Example 1 and Example 2, the oxygen and methane conversion of Reference 1 catalyst composition rapidly deteriorates with time on stream, which renders such catalyst unviable for commercial application whereas the inventive catalyst composition of Example 2 retains the desired oxygen and methane conversion property over a longer period of time on stream (even after 160 hours on stream). Thus, it is evident from the results on using Reference 2 catalyst and Reference 3 catalyst, and when compared with the results of Example 1 and Example 2, that it is the synergistic combination of the use of alkali metal promoters with metal oxide support, which imparts improved properties to the inventive catalyst compositions obtained from Example 1 and Example 2.

The present invention, therefore, provides a skilled person a catalyst composition for oxidative coupling of methane, having one or more benefits of (i) high carbon efficiency and $C_{2+}$ hydrocarbon selectivity, and (ii) increased catalyst stability along with improved methane conversion and oxygen conversion, by the synergistic combination of an alkali metal promoter and a metal oxide support.

TABLE 10

Summary Carbon efficiency and CO$_2$ selectivity

|  | Composition Formula | Highest Carbon Efficiency (%) at time on stream less than 10 hours (initial period) | Lowest Carbon dioxide selectivity (%) at time on stream less 10 hours (initial period) |
| --- | --- | --- | --- |
| Comparative Reference 1 catalyst | Mn—Na$_2$WO$_4$/SiO$_2$ | 90.3 | 9.7 |
| Comparative Reference 2 catalyst | Na$_{1.0}$Sr$_{1.0}$La$_{0.5}$Nd$_{0.1}$Er$_{0.3}$O$_x$ | 86.0 | 14.0 |
| Comparative Reference 3 catalyst | Sr$_{0.5}$La$_{1.8}$Nd$_{0.7}$Yb$_{0.1}$O$_x$/Al$_2$O$_3$ | 83.0 | 17.0 |
| Inventive composition Example 1 | (Na$_{4.0}$Sr$_{0.5}$La$_{1.8}$Nd$_{0.7}$Yb$_{0.1}$O$_x$)/Al$_2$O$_3$ | 88.0 | 12.0 |
| Inventive composition Example 2 | (Na$_{1.0}$Sr$_{0.5}$La$_{1.8}$Nd$_{0.7}$Yb$_{0.1}$O$_x$)/Al$_2$O$_3$ | 87.7 | 12.3 |

TABLE 10-continued

Summary Carbon efficiency and $CO_2$ selectivity

| | Composition Formula | Highest Carbon Efficiency (%) at time on stream less than 10 hours (initial period) | Lowest Carbon dioxide selectivity (%) at time on stream less 10 hours (initial period) |
|---|---|---|---|
| Inventive composition Example 3 | $(Na_{1.0}Sr_{0.5}La_{1.8}Nd_{0.7}Yb_{0.1}O_x)/Al_2O_3$ | 89.1 | 10.1 |

The invention claimed is:

1. A composition comprising a catalyst of the general formula represented by the empirical formula $Na_zSr_aLa_bNd_cYb_dO_x/Al_2O_3$, wherein 'a' ranges from about 0.1 to about 2; 'z' ranges from about 0.1 to about 8; 'b' ranges from about 0.6 to about 5; 'c' ranges from greater than zero to about 5; 'd' ranges from about greater than zero to about 0.4; and 'x' balances the oxidation state.

2. The composition according to claim 1, wherein the catalyst is represented by the empirical formula $Na_{4.0}Sr_{0.5}La_{1.8}Nd_{0.7}Yb_{0.1}O_x/Al_2O_3$.

3. The composition according to claim 1, wherein the catalyst is represented by the empirical formula $Na_{1.0}Sr_{0.5}La_{1.8}Nd_{0.7}Yb_{0.1}O_x/Al_2O_3$.

4. A method for preparing the composition of claim 1, the method comprising:
   a. impregnating an alumina ($Al_2O_3$) support with a solution comprising a sodium compound and forming a sodium impregnated alumina support precursor;
   b. calcining the sodium impregnated alumina support precursor at a temperature of at least 800° C. and for at least 1 hour, and forming a sodium impregnated alumina support;
   c. impregnating the sodium impregnated alumina support with an aqueous solution of a mixed metal oxide precursor comprising Sr, La, Nd, and Yb and forming a supported catalyst precursor; and
   d. calcining the supported catalyst precursor at a temperature of at least 800° C. and for at least 1 hour, and forming the composition.

5. A process for producing a $C_{2+}$ hydrocarbon mixture product, comprising:
   (a) introducing a feed mixture comprising methane and oxygen in a reactor containing the composition of claim 1;
   (b) subjecting the feed mixture to a methane coupling reaction under conditions suitable to produce the $C_{2+}$ hydrocarbon mixture product; and
   (c) recovering the $C_{2+}$ hydrocarbon mixture product after removing unconverted methane from the $C_{2+}$ hydrocarbon mixture product.

6. The process of claim 5, wherein the feed mixture has a molar ratio of methane to oxygen ranging from about 2:1 to about 15:1.

* * * * *

UNITED STATES PATENT AND TRADEMARK OFFICE
CERTIFICATE OF CORRECTION

PATENT NO. : 11,986,800 B2
APPLICATION NO. : 17/785216
DATED : May 21, 2024
INVENTOR(S) : Wugeng Liang et al.

It is certified that error appears in the above-identified patent and that said Letters Patent is hereby corrected as shown below:

In the Specification

Column 10 Line 44 replace "$500_{h-1}$" with -- $500\ h^{-1}$ --

Column 10 Line 47 replace "$400,000_{h-1}$" with -- $400,000\ h^{-1}$ --

Signed and Sealed this
Third Day of September, 2024

Katherine Kelly Vidal
*Director of the United States Patent and Trademark Office*